(12) United States Patent
Stopek et al.

(10) Patent No.: US 8,579,924 B2
(45) Date of Patent: Nov. 12, 2013

(54) IMPLANTABLE DEVICES INCLUDING A MESH AND A PIVOTABLE FILM

(75) Inventors: Joshua Stopek, Guilford, CT (US);
Amin Elachchabi, Hamden, CT (US);
Daniel Broom, Branford, CT (US);
Garrett Ebersole, New Haven, CT (US);
Ryan Witherell, Glastonbury, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/551,010

(22) Filed: Jul. 17, 2012

(65) Prior Publication Data

US 2013/0030360 A1    Jan. 31, 2013

Related U.S. Application Data

(60) Provisional application No. 61/511,686, filed on Jul. 26, 2011.

(51) Int. Cl.
*A61B 17/03* (2006.01)
*A61F 2/02* (2006.01)

(52) U.S. Cl.
USPC ............ 606/151; 623/11.11; 604/93.01

(58) Field of Classification Search
USPC ......... 623/11.11, 13.18, 13.19, 23.71–23.72, 623/23.74–23.76; 600/37; 606/151
See application file for complete search history.

(56) References Cited

U.S. PATENT DOCUMENTS

| | | | |
|---|---|---|---|
| 3,054,406 A | 9/1962 | Usher | |
| 4,931,546 A | 6/1990 | Tardy et al. | |
| 5,026,398 A * | 6/1991 | May et al. | ............ 623/13.11 |
| 5,147,374 A | 9/1992 | Fernandez | |
| 5,195,542 A | 3/1993 | Gazielly et al. | |
| 5,254,133 A | 10/1993 | Seid | |
| 5,258,000 A | 11/1993 | Gianturco | |
| 5,368,602 A | 11/1994 | de la Torre | |
| 5,370,650 A | 12/1994 | Tovey et al. | |
| 5,593,441 A * | 1/1997 | Lichtenstein et al. | ............ 600/37 |
| 5,634,931 A | 6/1997 | Kugel | |
| 5,695,525 A | 12/1997 | Mulhauser et al. | |
| 5,702,416 A | 12/1997 | Kieturakis et al. | |
| 5,711,960 A | 1/1998 | Shikinami | |
| 5,743,917 A | 4/1998 | Saxon | |
| 5,766,246 A | 6/1998 | Mulhauser et al. | |
| 5,769,864 A | 6/1998 | Kugel | |
| 5,916,225 A | 6/1999 | Kugel | |
| 5,922,026 A | 7/1999 | Chin | |
| 6,042,534 A | 3/2000 | Gellman et al. | |
| 6,120,539 A | 9/2000 | Eldridge et al. | |
| 6,162,962 A | 12/2000 | Hinsch et al. | |
| 6,171,318 B1 | 1/2001 | Kugel et al. | |
| 6,176,863 B1 * | 1/2001 | Kugel et al. | ............ 606/151 |
| 6,180,848 B1 | 1/2001 | Flament et al. | |
| 6,210,439 B1 | 4/2001 | Firmin et al. | |
| 6,214,020 B1 | 4/2001 | Mulhauser et al. | |
| 6,224,616 B1 | 5/2001 | Kugel | |

(Continued)

FOREIGN PATENT DOCUMENTS

| | | |
|---|---|---|
| FR | 2601371 A1 | 1/1988 |
| WO | WO 2006/020922 A2 | 2/2006 |
| WO | WO 2010/093333 A1 | 8/2012 |

*Primary Examiner* — Quynh-Nhu H Vu

(57) ABSTRACT

The present disclosure relates to implantable medical devices which include at least one mesh and at least one film pivotably attached to the mesh.

21 Claims, 8 Drawing Sheets

(56) References Cited

U.S. PATENT DOCUMENTS

| | | |
|---|---|---|
| 6,241,768 B1 | 6/2001 | Agarwal et al. |
| 6,258,124 B1 * | 7/2001 | Darois et al. ............... 623/14.13 |
| 6,267,772 B1 | 7/2001 | Mulhauser et al. |
| 6,270,530 B1 | 8/2001 | Eldridge et al. |
| 6,280,453 B1 | 8/2001 | Kugel et al. |
| 6,287,316 B1 | 9/2001 | Agarwal et al. |
| 6,290,708 B1 | 9/2001 | Kugel et al. |
| 6,306,079 B1 | 10/2001 | Trabucco |
| 6,319,264 B1 | 11/2001 | Törmälä et al. |
| 6,383,201 B1 | 5/2002 | Dong |
| 6,425,924 B1 | 7/2002 | Rousseau |
| 6,447,551 B1 | 9/2002 | Goldmann |
| 6,485,503 B2 | 11/2002 | Jacobs et al. |
| 6,596,002 B2 | 7/2003 | Therin et al. |
| 6,610,006 B1 | 8/2003 | Amid et al. |
| 6,616,685 B2 | 9/2003 | Rousseau |
| 6,645,226 B1 | 11/2003 | Jacobs et al. |
| 6,669,735 B1 | 12/2003 | Pelissier |
| 6,712,859 B2 | 3/2004 | Rousseau et al. |
| 6,736,823 B2 | 5/2004 | Darois et al. |
| 6,736,854 B2 | 5/2004 | Vadurro et al. |
| 6,755,868 B2 | 6/2004 | Rousseau |
| 6,790,213 B2 * | 9/2004 | Cherok et al. ............... 606/151 |
| 6,800,082 B2 | 10/2004 | Rousseau |
| 6,872,227 B2 | 3/2005 | Sump et al. |
| 6,926,723 B1 | 8/2005 | Mulhauser et al. |
| 7,011,688 B2 | 3/2006 | Gryska et al. |
| 7,021,086 B2 | 4/2006 | Ory et al. |
| 7,070,558 B2 * | 7/2006 | Gellman et al. ............... 600/37 |
| 7,087,065 B2 | 8/2006 | Ulmsten et al. |
| 7,094,261 B2 | 8/2006 | Zotti et al. |
| 7,101,381 B2 | 9/2006 | Ford et al. |
| 7,156,858 B2 | 1/2007 | Schuldt-Hempe et al. |
| 7,331,199 B2 | 2/2008 | Ory et al. |
| 7,393,319 B2 | 7/2008 | Merade et al. |
| 7,404,819 B1 | 7/2008 | Darios et al. |
| 7,556,598 B2 | 7/2009 | Rao |
| 7,594,921 B2 | 9/2009 | Browning |
| 7,722,527 B2 * | 5/2010 | Bouchier et al. ............... 600/30 |
| 7,785,334 B2 | 8/2010 | Ford et al. |
| 7,806,905 B2 | 10/2010 | Ford et al. |
| 8,123,817 B2 | 2/2012 | Intoccia et al. |
| 2002/0099344 A1 | 7/2002 | Hessel et al. |
| 2004/0215219 A1 | 10/2004 | Eldridge et al. |
| 2005/0240261 A1 | 10/2005 | Rakos et al. |
| 2005/0245787 A1 * | 11/2005 | Cox et al. ............... 600/37 |
| 2006/0253203 A1 | 11/2006 | Alvarado |
| 2007/0129736 A1 | 6/2007 | Solecki |
| 2007/0198040 A1 | 8/2007 | Buevich et al. |
| 2007/0260268 A1 | 11/2007 | Bartee et al. |
| 2007/0299538 A1 * | 12/2007 | Roeber ............... 623/23.72 |
| 2008/0109017 A1 | 5/2008 | Herweck et al. |
| 2008/0113001 A1 | 5/2008 | Herweck et al. |
| 2008/0118550 A1 | 5/2008 | Martakos et al. |
| 2008/0147200 A1 | 6/2008 | Rousseau et al. |
| 2008/0172071 A1 | 7/2008 | Barker |
| 2008/0255593 A1 | 10/2008 | St-Germain |
| 2009/0036996 A1 | 2/2009 | Roeber |
| 2009/0069826 A1 | 3/2009 | Walther et al. |
| 2009/0082792 A1 * | 3/2009 | Koyfman et al. ............... 606/151 |
| 2009/0105526 A1 * | 4/2009 | Piroli Torelli et al. ............... 600/30 |
| 2009/0125107 A1 | 5/2009 | Maxwell |
| 2009/0163936 A1 | 6/2009 | Yang et al. |
| 2009/0171377 A1 | 7/2009 | Intoccia et al. |
| 2009/0192530 A1 | 7/2009 | Adzich et al. |
| 2009/0198260 A1 | 8/2009 | Ford et al. |
| 2009/0270999 A1 | 10/2009 | Brown |
| 2009/0276057 A1 | 11/2009 | Trabucco et al. |
| 2009/0326676 A1 | 12/2009 | Dupic et al. |
| 2010/0286716 A1 | 11/2010 | Ford et al. |
| 2011/0118851 A1 * | 5/2011 | Eldridge et al. ............... 623/23.74 |
| 2011/0144667 A1 | 6/2011 | Horton et al. |
| 2011/0265283 A1 | 11/2011 | Duncan |
| 2012/0253472 A1 * | 10/2012 | Priewe ............... 623/23.72 |

* cited by examiner

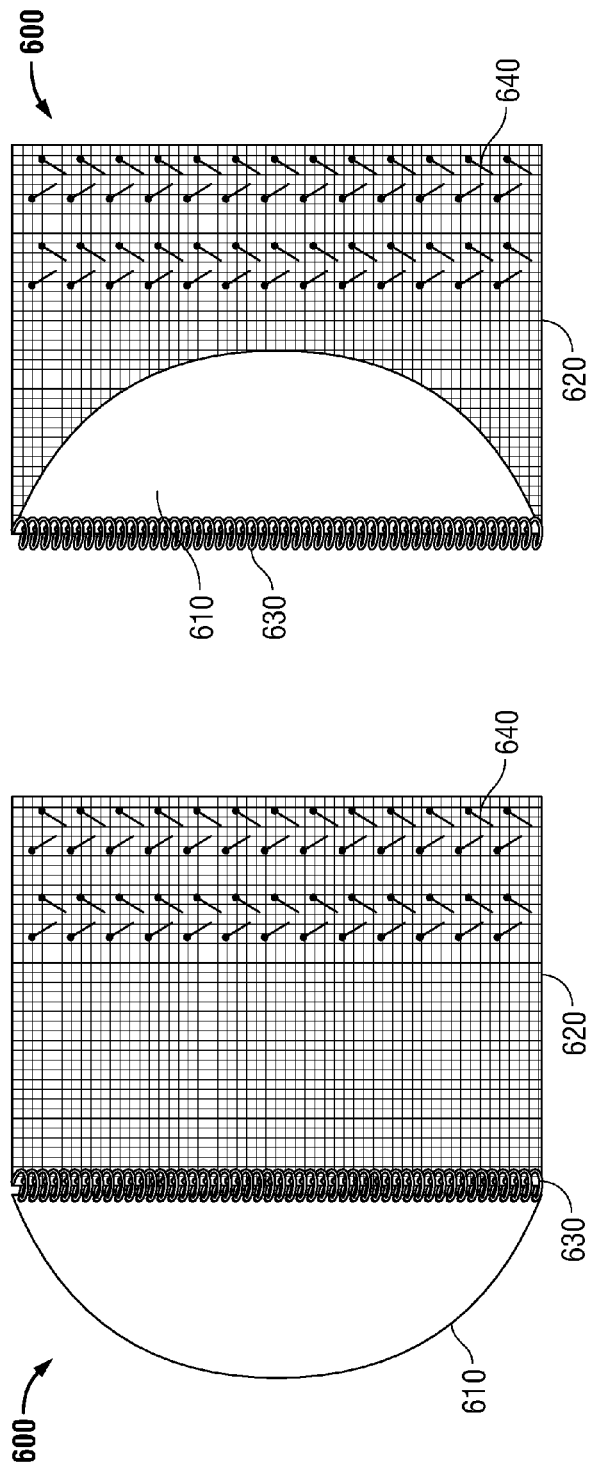
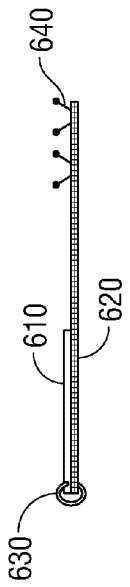
FIG. 6B
FIG. 6A
FIG. 6C

IMPLANTABLE DEVICES INCLUDING A MESH AND A PIVOTABLE FILM

CROSS-REFERENCE TO RELATED APPLICATIONS

The present application claims priority to, and the benefit of, U.S. Provisional Patent Application Ser. No. 61/511,686, filed on Jul. 26, 2011, the entire contents of which are hereby incorporated by reference.

BACKGROUND

1. Technical Field

The present disclosure relates generally to implantable medical devices, and more particularly, to implantable medical devices which include at least one mesh pivotably attached to at least one film, wherein the film is pivotable between a first position and a second position.

2. Background of Related Art

Surgical meshes may be used during both laparoscopic and open surgery for repair of many types of defects and injuries. For example, surgical meshes are commonly used in the repair of hernias. The meshes may be used to provide support to surrounding tissue.

During hernia repair, a mesh may be placed over the entirety of damaged tissue and some of the healthy tissue surrounding the defect. The mesh can be held in place by a fixation device that attaches the mesh to the surrounding tissue. A variety of different fixation devices may be used to anchor the mesh into the tissue. For example, a needled suture may be passed through the mesh and the tissue to hold the mesh in a position which spans the injured tissue. In other instances, staples, tacks, clips and pins may also be passed through the mesh and the tissue near the defect to anchor the implant in a position which spans the injured tissue.

Unfortunately, the use of such fixation devices may damage or weaken the mesh. In some instances wherein the mesh further includes an additional layer such as a film, the use of such fixation devices may also damage and/or weaken the film. Since known films are permanently attached to at least one side of the mesh, passage of the fixation device through the mesh and into the tissue, also forces the fixation device through the attached film. Although troubling for any film material, the damage inflicted by the fixation devices upon films designed to prevent adhesion may be most troubling, since such damage may create opportunities for the ingrowth of tissue and the formation of unwanted adhesions and scar tissue. In addition, multilayer implants may require the surgical personnel to alter the use of certain fixation devices to accommodate the thickness of such multilayer implants wherein the film is permanently attached to the mesh.

Although methods that require the use of fixation devices have been proven effective in anchoring such multilayer implants into the tissue, penetration of the additional layers by such devices may weaken or damage the overall strength of the implant, as well as the implants ability to deliver therapeutic agents, and/or prevent tissue adhesions. Thus, implantable devices which allow for the mesh to be secured into the tissue separately from the additional layers is desirable in order to further limit the amount of trauma to the additional film layers.

SUMMARY

Accordingly, the present disclosure relates to implantable medical devices which include a surgical mesh pivotably connected to a polymeric film. The mesh may generally be a textile or fabric created to promote tissue ingrowth and support injured tissue. The film may generally be polymeric in nature and may be intended to further enhance the ingrowth of tissue into the implant, prevent adhesions of surrounding tissue, deliver therapeutic agents and/or simply provide addition support to the implant. In certain embodiments, at least a portion of the film is fixedly attached to the mesh. In certain embodiments, the film may be connected to the mesh via a pivot member. In other embodiments, the implantable medical device further includes at least one therapeutic agent. In still other embodiments, the film may be a single layer. In yet other embodiments, the film may include multiple polymeric layers.

Methods of forming such devices are also disclosed.

BRIEF DESCRIPTION OF THE DRAWINGS

The foregoing objects and advantages of the disclosure will become more apparent from the reading of the following description in connection with the accompanying drawings, in which:

FIGS. 6A and 6B are a top view and side view, respectively, of an implantable medical device a second open position according to one embodiment described in the present disclosure;

FIG. 6C is a side view of the implantable device of FIGS. 6A, 6B, in a first open position according to one embodiment described in the present disclosure;

DETAILED DESCRIPTION

Figure 1A:
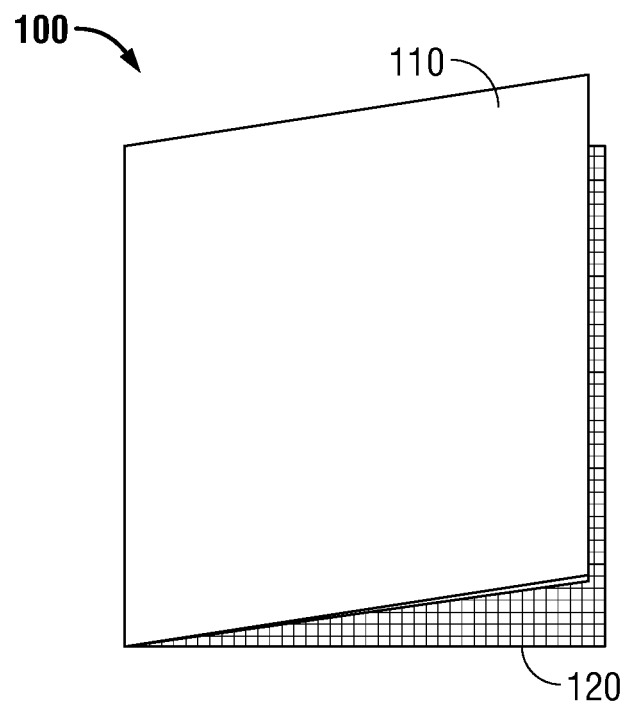
FIGS. 1A and 1B are a perspective view and side view, respectively, of an implantable medical device a first closed position according to one embodiment described in the present disclosure.

The present disclosure relates to implantable medical devices which include a surgical mesh pivotably connected to a film. By pivotable, the film is repositionable between a first position wherein the film covers at least a first side of the mesh and a second position wherein the film does not cover at least a first side of the mesh. In certain embodiments, at least a portion of the film is fixedly attached to the mesh. In certain embodiments, the film may be connected to the mesh via a pivot member. In other embodiments, the implantable medical device further includes at least one therapeutic agent.

By implantable, the medical devices described herein may be positioned, for any duration of time, at a location within a body, such as within a portion of the abdominal cavity. Furthermore, the terms "implantation" and "implanted" refer to the positioning, for any duration of time, of a medical device at a location within a body, such as within a portion of the abdominal cavity.

The implantable medical devices described herein include at least one surgical mesh. The surgical mesh described herein may include porous fabrics made from intertwined filaments. The filaments may extend horizontally and vertically in a manner which produces sections where the filaments crossover one another creating points of common intersection. The surgical mesh may be woven, non-woven, knitted or braided. In some embodiments, the filaments may form two-dimensional or three-dimensional meshes. Some examples of two-dimensional and/or three-dimensional mesh substrates may be found in U.S. Pat. No. 7,021,086, U.S. Pat. No. 6,596,002, U.S. Pat. No. 7,331,199, the entire contents of which are incorporated by reference herein.

Suitable meshes for use in the present disclosure include, for example, a collagen composite mesh such as PARIETEX™ Composite Mesh (commercially available from Tyco Healthcare Group LP, d/b/a Covidien). PARIETEX™ Composite Mesh is a 3-dimensional polyester weave with a resorbable collagen film bonded on one side. Another suitable mesh includes Parietex Progrip™ self-fixating mesh (also commercially available from Covidien). Parietex Progrip™ is a polyester mesh which includes poly lactic acid (PLA) grip members. Other suitable meshes include those sold under the names PARIETENE®, PARIETEX™, SURGIPRO™ (all commercially available from Covidien); PROLENE™ (commercially available from Ethicon, Inc.); MARLEX®, DULEX®, 3D MAX® mesh, PERFIX® plug, VENTRALEX®, and KUGEL® patch (all commercially available from C.R. Bard, Inc.); PROLITE™, PROLITE ULTRA™ (all commercially available from Atrium Medical); COMPOSIX®, SEPRAMESH®, and VISILEX® (all commercially available from Davol, Inc.); and DUALMESH®, MYCROMESH®, and INFINIT® mesh (all commercially available from W.L. Gore). Additionally, meshes within the scope and context of this disclosure may include biologic materials such as allografts (i.e., AlloDerm® Regenerative Tissue Matrix from Lifecell), autografts, and xenografts (i.e., PERMACOL™, from Covidien). In alternate embodiments, processed/purified tissues may also be employed.

In certain preferred embodiments, Parietex™ Composite Mesh or Parietex™ Pro-grip may be utilized in accordance with the present invention.

The mesh may include filaments such as monofilaments or multi-filaments and, in embodiments, a plurality of multi-filaments may be combined to form yarns. It is envisioned that the mesh may be configured to any size and/or shape suitable for hernia repair. Further, the filaments may comprise core/sheath constructs.

The medical devices described herein may be formed using any method within the purview of those skilled in the art. Some non-limiting examples include, weaving, knitting, braiding, crocheting, extruding, spraying, casting, molding, and combinations thereof. In embodiments, the medical device may include a two or three dimensional surgical mesh which is woven, knitted, braided, or crocheted.

In certain embodiments, the medical device may be a surgical mesh knitted on a warp knitting machine, of the tricot or Raschel type, with at least three sheets or warps of yarn and as many guide bars.

Figure 9:
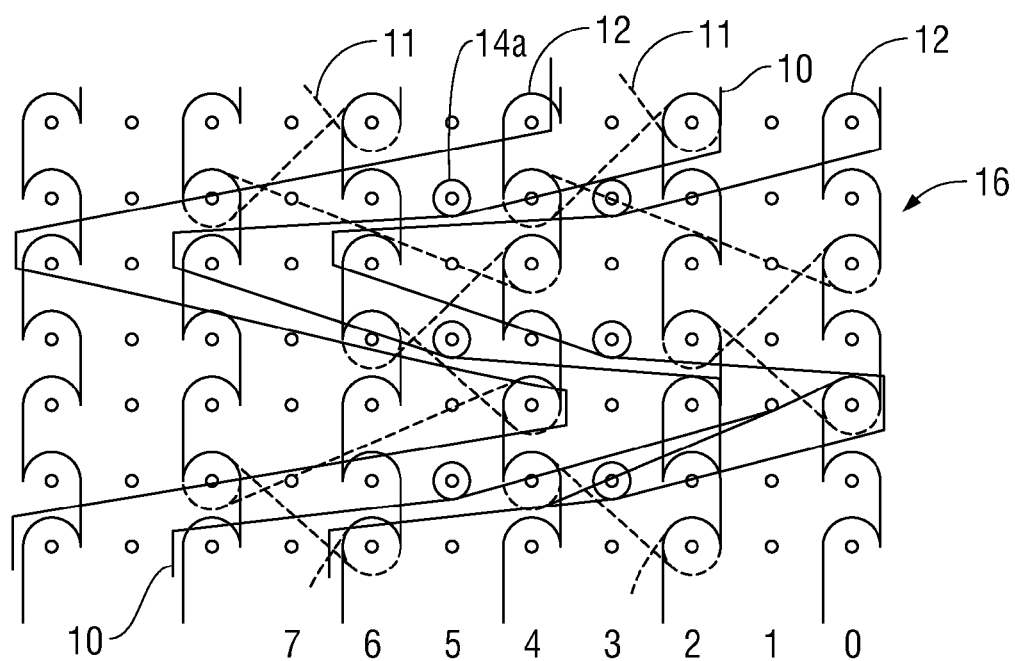
FIG. 9 is a diagram showing the weave of three sheets forming a medical device according to one embodiment described in the present disclosure.

In one embodiment, as illustrated in FIG. 9, a rear bar is threaded, one guide full and one guide empty, with first mono- or multi-filaments 10 of a biocompatible polymer as represented as a solid line. An intermediate bar is threaded, one guide full, three guides empty, with second mono- or multi-filaments 11 of a biocompatible polymer as represented as a broken line in FIG. 9. The intermediate bar works in such a way as to obtain a zigzag openwork pattern between the columns of meshes. Finally, a front bar is threaded, one guide full, one guide empty, and works in a chain stitch with third mono- or multi-filaments 12a biocompatible polymer as represented by a thin line in FIG. 9. The third filament 12, i.e., a chain stitch, imprisons first filament 10 and maintains the length of the mesh while contributing to the formation of the mesh with the intermediate sheet formed by the second filament 11. The different filaments may form yarns and may be worked according to the following chart:

| Warp | | |
|---|---|---|
| Rear bar I | Intermediate bar II | Front bar III |
| | Raschel | |
| Front bar I | Intermediate bar II | Rear bar III |
| 7 | 3 | 1 |
| 7 | 2 | 0 |
| 3 | 4 | 0 |
| 4 | 5 | 1 |
| 0 | 1 | |
| 0 | 0 | |
| 4 | 2 | |
| 3 | 3 | |
| | 1 | |
| | 0 | |
| | 4 | |
| | 5 | |

The rear bar places the first filament or yarn in partial weft under the chain stitch and "thrown" onto the needle not forming a chain stitch. For this reason, at the next row, the needle not forming a chain stitch not being supplied permits escape of the filament which forms a loop 14a projecting from the front face of the mesh.

The threading—one guide full, three guides empty—in the intermediate bar, associated with the displacement, makes it possible to form a light ground texture, stable in width, and open-worked to permit good tissue integration.

The mesh 14 thus obtained may be provided with loops 14a (FIG. 10) which may be perpendicular to one of the mesh surfaces. Loops 14a may also include a rigidity and hold at a right angle which may be obtained by the rigidity or nerve of the filaments employed. This rigidity may be necessary for the subsequent formation of grip members which ensure a grip function to at least a portion of the implantable medical device.

Figure 10:
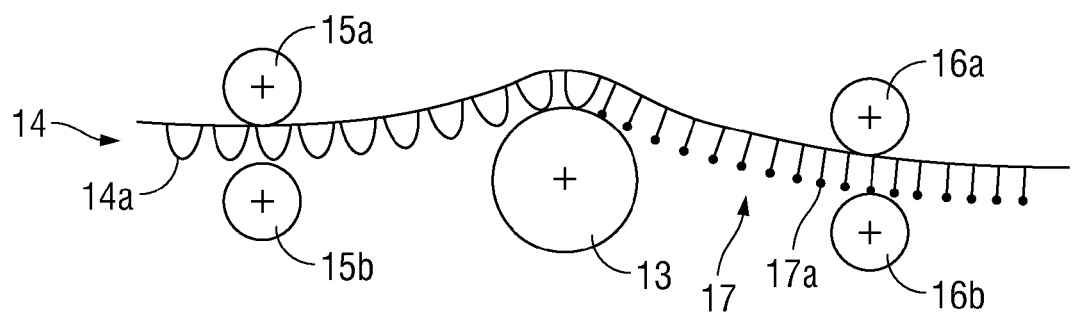
FIG. 10 is a diagrammatic side view of a device permitting the formation of spiked naps on the medical device of FIG. 9 according to another embodiment described in the present disclosure.

On leaving the loom, mesh 14 may be subjected to a thermosetting operation which stabilizes the mesh length and width. The mesh may then be subjected to a phase of formation of the grip members consisting, as is shown in FIG. 10, in passing the mesh over a cylinder 13 containing an electrical heating resistor. Mesh 14 is pressed flat on cylinder 13 by two pairs of rollers, upstream 15a, 15b and downstream 16a, 16b, respectively, which are vertically displaceable for controlling this pressing force.

This control as well as that of the temperature of the resistor placed in cylinder 13 and of the speed of movement of mesh 14 across cylinder 13 make it possible to melt the head of each of loops 14a so that each loop 14a forms two grip members 17.

Each grip member 17 thus may have a substantially rectilinear body protruding perpendicularly with respect to mesh 14 and, at the free end of this body, a head 17a of greater width than that of the body. Head 17a has a generally spheroidal shape or a mushroom shape. Grip member 17 gives mesh 14 the ability to attach to tissue when implanted. In addition, grip members 17 may attach to other portions of mesh 14 when folded or rolled. The grip members may be positioned along any portion of the mesh and in any quantity and/or configuration. For example, in some embodiments, the grip members may be positioned on the same portion of the mesh as the film. In other embodiments, the grip members may be positioned on a different portion of the mesh which does not include the film.

Any biocompatible material may be used to form the mesh described herein. For example, the mesh may be made from non-bioabsorbable materials, such as polypropylene, polyethylene terephthalate, polytetrafluoroethylene, and the like. In other examples, the mesh may be made from bioabsorbable materials, such as polylactide, polyglycolide, polycaprolactone, polydioxanone, polysaccharides and the like. In embodiments, the mesh may be made from a combination of absorbable and non-bioabsorbable materials.

The medical devices described herein also include a polymeric film layer which may be made from a biocompatible material. The biocompatible material may be a homopolymer or a copolymer, including random copolymer, block copolymer, or graft copolymer. The biocompatible material may be a linear polymer, a branched polymer, or a dendrimer. The biocompatible material may be of natural or synthetic origin and may be bioabsorbable or non-bioabsorbable.

Some non-limiting examples of bioabsorbable materials used to form the film include polymers selected from the group consisting of aliphatic polyesters; polyamides; polyamines; polyalkylene oxalates; poly(anhydrides); polyamidoesters; copoly(ether-esters); poly(carbonates) including tyrosine derived carbonates; poly(hydroxyalkanoates) such as poly(hydroxybutyric acid), poly(hydroxyvaleric acid), and poly(hydroxybutyrate); polyimide carbonates; poly(imino carbonates) such as such as poly(bisphenol A-iminocarbonate and the like); polyorthoesters; polyoxaesters including those containing amine groups; polyphosphazenes; poly(propylene fumarates); polyurethanes; polymer drugs such as polydiflunisol, polyaspirin, and protein therapeutics; biologically modified (e.g., protein, peptide) bioabsorbable polymers; and copolymers, block copolymers, homopolymers, blends, and combinations thereof.

More specifically, aliphatic polyesters include, but are not limited to, homopolymers and copolymers of lactide (including lactic acid, D-,L- and meso lactide); glycolide (including glycolic acid); epsilon-caprolactone, p-dioxanone (1,4-dioxan-2-one); trimethylene carbonate (1,3-dioxan-2-one); alkyl derivatives of trimethylene carbonate; Δ-valerolactone; β-butyrolactone; γ-butyrolactone; ε-decalactone; hydroxybutyrate; hydroxyvalerate; 1,4-dioxepan-2-one (including its dimer 1,5,8,12-tetraoxacyclotetradecane-7,14-dione); 1,5-dioxepan-2-one; 6,6-dimethyl-1,4-dioxan-2-one; 2,5-diketomorpholine; pivalolactone; α,α diethylpropiolactone; ethylene carbonate; ethylene oxalate; 3-methyl-1,4-dioxane-2,5-dione; 3,3-diethyl-1,4-dioxan-2,5-dione; 6,8-dioxabicycloctane-7-one; and polymer blends and copolymers thereof.

In certain embodiments, the hydrophobic polymers of the films may include homopolymers or copolymers which include lactide, glycolide, dioxanone, trimethylene carbonate, and ε-caprolactone. For example, the therapeutic agents described herein may be combined with copolymers, i.e., random, or block copolymers, of lactide and glycolide or glycolide and ε-caprolactone. Increasing the amount of glycolide may increase the films degradation rate. While increasing the amount of lactide and/or caprolactone may extend the degradation/absorption profile of the film. For example, lactide rich copolymers, i.e., greater than about 50% lactide, may be particularly useful to enhance a particular polymer's solubility, such as glycolide. Other suitable bioabsorbable materials may include but are not limited to poly(amino acids) including proteins such as collagen (I, II and III), elastin, fibrin, fibrinogen, silk, and albumin; peptides including sequences for laminin and fibronectin (RGD); polysaccharides such as hyaluronic acid (HA), dextran, alginate, chitin, chitosan, and cellulose; glycosaminoglycan; mucilage, pectin; and combinations thereof.

The term "collagen" is meant to include any type of collagen, whether natural or synthetic, of human or animal origin, such as, for example, enriched human collagen of type I, human collagen of type III, also enriched, human collagen of type I+III or of type IV or other collagens such as animal collagen of type I or of type I+III. The collagen may be oxidized or non-oxidized.

In certain embodiments, the collagen may be oxidized without crosslinking. For example, native collagen may be dipped in an acid solution and/or washed, to eliminate the telopeptides, notably by pepsin digestion.

The collagen may also be modified by oxidative cleavage. For this purpose periodic acid or one of its salts can be used, applying the technique described by M. TARDY et al. (FR-A-2 601 371 and U.S. Pat. No. 4,931,546, the entire contents of which are hereby incorporated by reference).

It is recalled briefly that this technique consists of mixing the collagen in acid solution with a solution of periodic acid or one of its salts at a concentration of between 1 and $10^{-5}$M, preferably between 5 $10^{-3}$ and $10^{-1}$M, at a temperature of between 10 and 25° C. for 10 minutes to 72 hours.

This process breaks down some of the collagen's components, these being hydroxylysine and the sugars, thus creating reactive sites without causing crosslinking.

The oxidative cleavage of collagen allows moderate cross-linking later in the collagenic material but does not exclude the possibility of providing this function by other means of moderate cross-linking, for example by beta or gamma irradiation, or other agents of moderate cross-linking, for example chemical reagents at suitably low and non-toxic doses.

For some applications, the polymer film layers described herein may include collagen which is not oxidized or a mixture in any proportions of non-oxidized and oxidized collagens.

Additionally, synthetically modified natural polymers such as cellulose and polysaccharide derivatives, including alkyl celluloses, hydroxyalkyl celluloses, cellulose ethers, cellulose esters, nitrocelluloses, and chitosan may be utilized. Examples of suitable cellulose derivatives include methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose (CMC), cellulose triacetate, and cellulose sulfate sodium salt. These may be collectively referred to herein, in embodiments, as "celluloses." In certain embodiments, the film layer may comprise carboxymethylcellulose.

Both the mesh and/or the film may further consist of at least one optional ingredient. Some examples of suitable optional ingredients include emulsifiers, viscosity enhancers, dyes, pigments, fragrances, pH modifiers, wetting agents, plasticizers, antioxidants, and the like. The optional ingredients may represent up to about 10% of the mesh and/or film by weight.

In some embodiments, the film may include at least one plasticizer, i.e., glycerol, PEG, etc. For instance, in some embodiments, the film may include a combination of carboxymethylcellulose and glycerol. In other embodiments, the film may include collagen and at least one of PEG and glycerol.

The films described herein may be formed by any suitable method known to those skilled in the art. In certain embodiments, a solution may be formed which includes the suitable polymeric material and any optional ingredients. The solution may be cast bulk sheet stock, sprayed using an ultrasonic sprayer, extruded, molded and the like, to form the films described herein.

In certain embodiments, the polymeric film may be formed using an ultrasonic spraying nozzle onto an inert substrate. Spraying films results in a unique ability to include a high therapeutic payload of a therapeutic agent. For example, the medical device as described herein may be fabricated by passing a first solution containing a hydrophobic polymer and a second solution containing a therapeutic agent through an ultrasonic spray nozzle to form droplets. The droplets may be mixed while falling towards or being deposited onto an inert substrate, such as silicone sheet, or a portion of the mesh to form a film. In some embodiments, prior to spraying the film, an inert substrate may be positioned on the portion of the mesh which the film is not meant to become fixedly attached to. Thus, upon formation of the film, the film may adhere to the portions of the mesh which are not covered by the inert substrate and the film will not fixedly attach to the portions of the mesh which are covered by the inert substrate.

Alternatively, the film may be cast directly on a portion of the mesh surface, optionally utilizing an inert substrate disposed between the film and the mesh. In other embodiments, the film may be formed directly on a portion of the mesh. In still other embodiments, the film may be formed before being connected to the mesh. In yet another embodiment, the film may be combined with the pivot member before being combined with the mesh.

In some embodiments, the films include a single layer containing a hydrophobic polymer and a therapeutic agent. In other embodiments, the films include a first layer containing a hydrophobic polymer and a second layer containing a therapeutic agent. In still other embodiments, the films include a tri-layer structure wherein a second layer containing a therapeutic agent is positioned between a first layer containing a hydrophobic polymer and a third layer containing the same or different hydrophobic polymer.

The hydrophobic polymers used to form the films may initially form polymer solutions, including suspensions, emulsions, dispersions and the like, prior to being passed through an ultrasonic sprayer. Some non-limiting examples of solvents suitable for forming the polymer solutions may include methylene chloride, chloroform, N-methylpyrrolidone, tetrahydrofuran, dimethylformamide, methanol, ethanol, hexanes, acetone and combinations thereof. The polymer may represent from about 1.0% to about 50% (w/w) in the solution.

In some embodiments, the solvent used to form the hydrophobic polymer solution may not be the same solvent used to form the therapeutic agent solution. In some embodiments, the therapeutic agent is not miscible in the solvent used to form the polymer solution.

The term "therapeutic agent", as used herein, is used in its broadest sense and includes any substance or mixture of substances that provides a beneficial, therapeutic, pharmacological, and/or prophylactic effect. The agent may be a drug which provides a pharmacological effect.

The term "drug" is meant to include any agent capable of rendering a therapeutic affect, such as, anti-adhesives, antimicrobials, analgesics, antipyretics, anesthetics (e.g. local and systemic), antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, platelet activating drugs, clotting factors, and enzymes. It is also intended that combinations of agents may be used.

Other therapeutic agents, which may be included as a drug include: anti-fertility agents; parasympathomimetic agents; psychotherapeutic agents; tranquilizers; decongestants; sedative hypnotics; sulfonamides; sympathomimetic agents; vaccines; vitamins; antimalarials; anti-migraine agents; anti-parkinson agents such as L-dopa; anti-spasmodics; anticholinergic agents (e.g., oxybutynin); antitussives; bronchodilators; cardiovascular agents, such as coronary vasodilators and nitroglycerin; alkaloids; analgesics; narcotics such as codeine, dihydrocodeinone, meperidine, morphine and the like; non-narcotics, such as salicylates, aspirin, acetaminophen, d-propoxyphene and the like; opioid receptor antagonists, such as naltrexone and naloxone; anti-cancer agents; anti-convulsants; anti-emetics; antihistamines; anti-inflammatory agents, such as hormonal agents, hydrocortisone, prednisolone, prednisone, non-hormonal agents, allopurinol, indomethacin, phenylbutazone and the like; prostaglandins and cytotoxic drugs; chemotherapeutics; estrogens; antibacterials; antibiotics; anti-fungals; anti-virals; anticoagulants; anticonvulsants; antidepressants; and immunological agents.

Other examples of suitable agents, which may be included in the films described herein include, for example, viruses and cells; peptides, polypeptides and proteins, as well as analogs, muteins, and active fragments thereof; immunoglobulins; antibodies; cytokines (e.g., lymphokines, monokines, chemokines); blood clotting factors; hemopoietic factors; interleukins (e.g., IL-1, IL-3, IL-4, IL-6); interferons (e.g., β-IFN, α-IFN and γ-IFN); erythropoietin; nucleases; tumor necrosis factor; colony stimulating factors (e.g., GCSF, GM-CSF, MCSF); insulin; anti-tumor agents and tumor suppressors; blood proteins such as fibrin, thrombin, fibrinogen, synthetic thrombin, synthetic fibrin, synthetic fibrinogen; gonadotropins (e.g., FSH, LH, CG, etc.); hormones and hormone analogs (e.g., growth hormone); vaccines (e.g., tumoral, bacterial and viral antigens); somatostatin; antigens; blood coagulation factors; growth factors (e.g., nerve growth factor, insulin-like growth factor); bone morphogenic proteins; TGF-B; protein inhibitors; protein antagonists; protein agonists; nucleic acids such as antisense molecules, DNA, RNA, and RNAi; oligonucleotides; polynucleotides; and ribozymes.

Some specific non-limiting examples of water-soluble drugs that may be used in the present polymeric films include, lidocaine, bupivacaine, tetracaine, procaine, dibucaine, sirolimus, taxol, chlorhexidine, polyhexamethylene, thiamylal sodium, thiopental sodium, ketamine, flurazepam, amobarbital sodium, phenobarbital, bromovalerylurea, chloral hydrate, phenyloin, ethotoin, trimethadione, primidone, ethosuximide, carbamazepine, valproate, acetaminophen, phenacetin, aspirin, sodium salicylate, aminopyrine, antipyrine, sulpyrine, mepirizole, tiaramide, perixazole, diclofenac, anfenac, buprenorphine, butorphanol, eptazocine, dimenhydrinate, difenidol, dl-isoprenaline, chlorpromazine, levomepromazine, thioridazine, fluphenazine, thiothixene, flupenthixol, floropipamide, moperone, carpipramine, clocapramine, imipramine, desipramine, maprotiline, chlordiazepoxide, clorazepate, meprobamate, hydroxyzine, saflazine, ethyl aminobenzoate, chlorphenesin carbamate, methocarbamol, acetylcholine, neostigmine, atropine, scopolamine, papaverine, biperiden, trihexyphenidyl, amantadine, piroheptine, profenamine, levodopa, mazaticol, diphenhydramine, carbinoxamine, chlorpheniramine, clemastine, aminophylline, choline, theophylline, caffeine, sodium benzoate, isoproterenol, dopamine, dobutamine, propranolol, alprenolol, bupranolol, timolol, metoprolol, procainamide, quinidine, ajmaline, verapamil, aprindine, hydrochlorothiazide, acetazolamide, isosorbide, ethacrynic acid, captopril, enalapril, delapril, alacepril, hydralazine, hexamethonium, clonidine, bunitrolol, guanethidine, bethanidine, phenylephrine, methoxamine, diltiazem, nicorandil, nicametate, nicotinic-alcohol tartrate, tolazoline, nicardipine, ifenprodil, piperidinocarbamate, cinepazide, thiapride, dimorpholamine, levallorphan, naloxone, hydrocortisone, dexamethasone, prednisolone, norethisterone, clomiphene, tetracycline, methyl salicylate, isothipendyl, crotamiton, salicylic acid, nystatin, econazole, cloconazole, vitamin $B_1$, cyclothiamine, vitamin $B_2$, vitamin $B_3$, vitamin $B_5$, vitamin $B_6$, vitamin $B_7$, vitamin $B_9$, vitamin $B_{12}$, vitamin C, nicotinic acid, folic acid, nicotinamide, calcium pantothenate, pantothenol, panthetin, biotin, ascorbic acid, tranexamic acid, ethamsylate, protamine, colchicine, allopurinol, tolazamide, glymidine, glybuzole, metoformin, buformin, orotic acid, azathioprine, lactulose, nitrogen mustard, cyclophophamide, thio-TEPA, nimustine, thioinosine, fluorouracil, tegafur, vinblastine, vincristine, vindesine, mitomycin C, daunorubicin, aclarubicin, procarbazine, cisplatin, methotrexate, benzylpenicillin, amoxicillin, penicillin, oxycillin, methicillin, carbenicillin, ampicillin, cefalexin, cefazolin, erythromycin, kitasamycin, chloramphenicol, thiamphenicol, minocycline, lincomycin, clindamycin, streptomycin, kanamycin, fradiomycin, gentamycin, spectinomycin, neomycin, vanomycin, tetracycline, ciprofloxacin, sulfanilic acid, cycloserine, sulfisomidine, isoniazid, ethambutol, acyclovir, gancyclovir, vidabarine, azidothymidine, dideoxyinosine, dideoxycytosine, morphine, codeine, oxycodone, hydrocodone, cocaine, pethidine, fentanyl, polymeric forms of any of the above drugs and any combinations thereof.

The water-soluble drug may not need to be converted to a salt form, i.e., tetracycline hydrochloride. In some embodiments, the therapeutic agent may include an anesthetic, i.e., bupivacaine, lidocaine, benzocaine, and the like.

Although the above therapeutic agents have been provided for the purposes of illustration, it should be understood that the present disclosure is not so limited. In particular, although certain therapeutic agents are specifically referred to above, the present disclosure should be understood to include analogues, derivatives and conjugates of such agents.

The therapeutic agent may be combined with any portion of the medical device, including the mesh, the film layer and/or the pivot member. In some embodiments, the therapeutic agent may be included in the polymeric film to provide sustained release of the therapeutic agent following implantation. Because the film may include a high payload of therapeutic agent, the polymeric films may provide sustained release of the agent for longer periods of time.

Figure 1B:
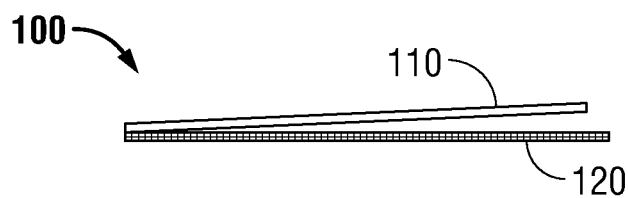

Turning now to FIGS. 1A and 1B, implantable medical device 100 is illustrated including film 110 pivotably attached to mesh 120 and in a first or closed position wherein a substantial portion of film 110 covers at least one side of mesh 120. Although film 110 is not shown in complete contact with mesh 120, it is envisioned that film 110 has the ability to cover mesh 120 completely in the first or closed position.

Figure 2A:
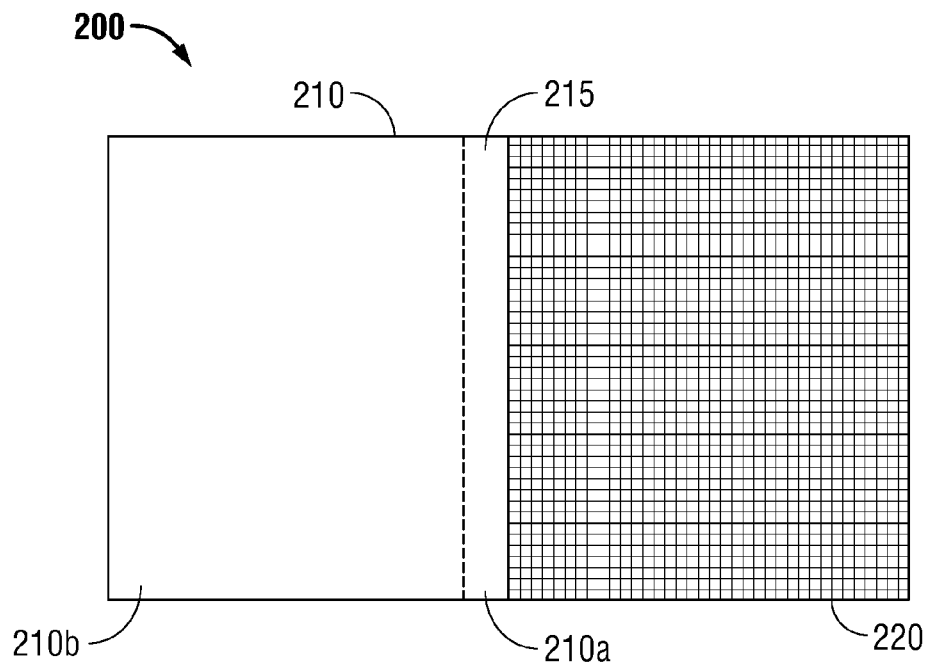
FIGS. 2A and 2B are a perspective view and side view, respectively, of an implantable medical device a second open position according to one embodiment described in the present disclosure.
Figure 2B:
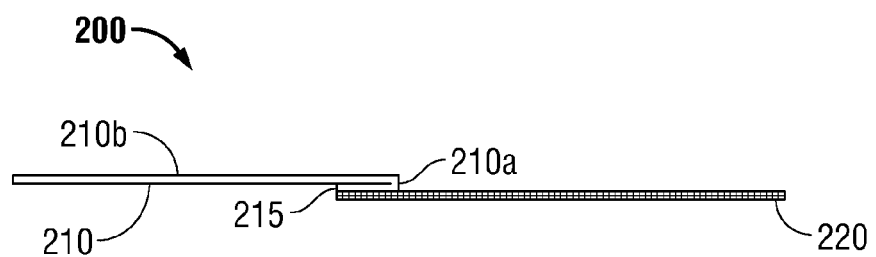

In FIGS. 2A and 2B, implantable medical device 200 is illustrated including film 210 pivotably attached to mesh 220 and in a second or open position wherein a substantial portion of film 210 is not attached to mesh 220 and does not cover at least one side of mesh 220. Film 210 includes first portion 210a which is fixedly attached to mesh 220 and second portion 210b which is free of mesh 220. First portion 210a of film 210 is fixedly attached to mesh 220 via connector 215. Connector 215 may represent any implantable material suitable and/or capable of securing first portion 210a to mesh 220. Some non-limiting examples include adhesives, sutures, staples, clips, and the like. In some embodiments, the connector may include an adhesive, such as a cyanoacrylate. In other embodiments, first portion 210a of film 210 may be fixedly attached to mesh 220 through increased pressure and/or energy, such as heat, to physically bond the two together.

Although film 210 is shown approximately parallel or 180° relative to mesh 220, it is envisioned that film 210 may be repositioned to any variety of angles α ranging from 0 to 360 degrees relative to mesh 220. In addition, although shown in a generally planar configuration, implantable medical device 200, including film 210 and/or mesh 220 are not intended to be limited to planar configurations only and may represent non-planar configurations as well.

Figure 3A:
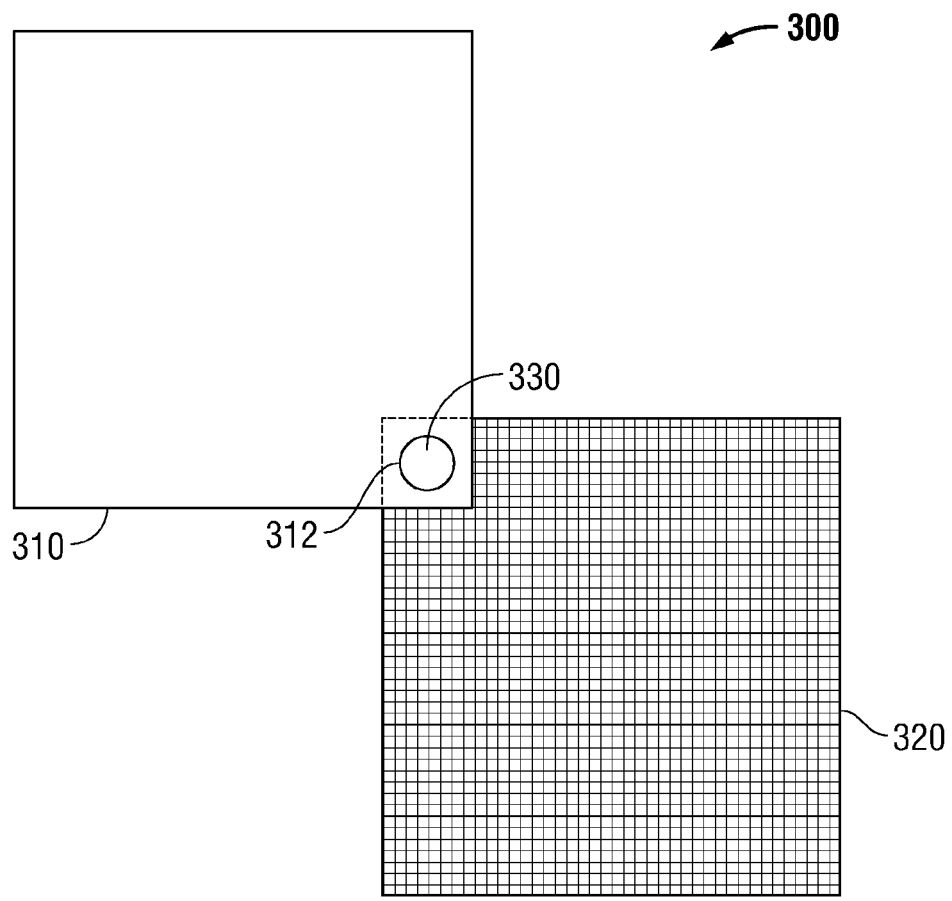
FIGS. 3A and 3B are a top view and side view, respectively, of an implantable medical device a second open position according to one embodiment described in the present disclosure.
Figure 3B:
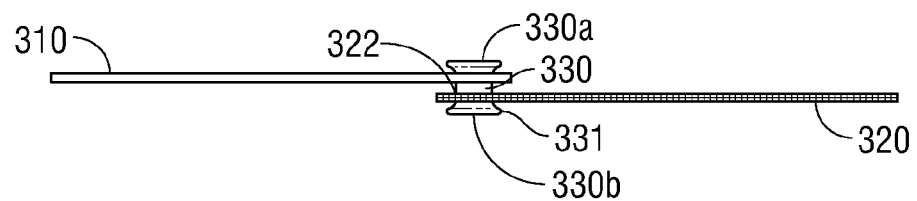

As depicted in FIGS. 3A and 3B, device 300 includes film 310 including aperture 312, mesh 320 including opening 322, and pivot member 330. Pivot member 330 passes through aperture 312 and opening 322 to pivotably connect film 310 to mesh 320. The diameter of aperture 312 and opening 322 may be the same or different, however, the diameter of each must be sufficient in size to accommodate pivot member 330. As illustrated in FIGS. 3A and 3B, pivot member 330 may represent a spool-shape wherein top portion 330a and bottom portion 330b of pivot member 330 include extensions 331 to increase the diameter at the top and bottom portions 330a, 330b, of pivot member 330 to frictionally hold film 310 and mesh 320 on pivot member 330.

Pivot member 330, like film 310 and mesh 320, may be made from any biocompatible material and in embodiments may be made from any bioabsorbable material, non-bioabsorbable, and/or combinations of such materials as previously described herein. It is envisioned that in some embodiments, pivot member 330 may remain as a portion of the implantable medical device and may be implanted into tissue. In other embodiments, it is envisioned that following implantation, pivot member 330 and/or some other portion of film 310 and/or mesh 320 may simply be detached from implantable medical device 300 prior to, during, or after implantation, and removed from the tissue.

Figure 4A:
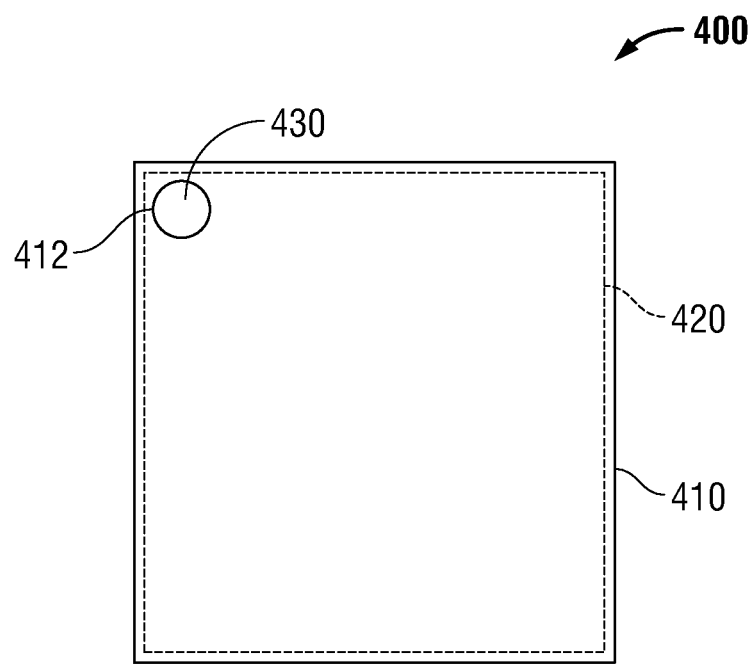
FIGS. 4A and 4B are a top view and side view, respectively, of an implantable medical device a first closed position according to one embodiment described in the present disclosure.
Figure 4B:
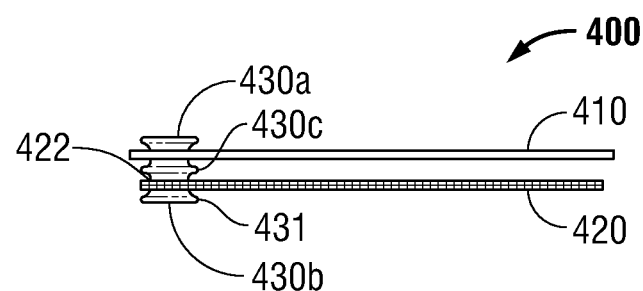

In FIGS. 4A and 4B, device 400 includes film 410 including aperture 412, mesh 420 including opening 422, and pivot member 430. Pivot member 430 passes through aperture 412 and opening 422 to pivotably connect film 410 to mesh 420. The diameter of aperture 412 and opening 422 may be the same or different, however, the diameter of each must be sufficient in size to accommodate pivot member 430. As illustrated in FIGS. 4A and 4B, pivot member 430 may represent a spool-shape wherein top portion 430a, bottom portion 430b, and middle portion 430c of pivot member 430 include extensions 431 to increase the diameter at the top, bottom, and middle portions 430a, 430b, 430c of pivot member 430 to frictionally hold film 410 and mesh 420 on pivot member 430. Middle portion 430c may be positioned between film 410 and mesh 420 to maintain separation of film 410 and mesh 420 in the area near pivot member 430 to enhance the ability of film 410 and mesh 420 to pivot.

As further shown in FIGS. 4A and 4B, in some embodiments, film 410 may be larger in area than mesh 420 thus extending past the outer edges of mesh 420. This configuration may be useful in hernia repair wherein film 410 represents an anti-adhesion barrier film. By extending past the outer perimeter of mesh 420, anti-adhesive film 410 may not only prevent adhesion alone the top side of mesh 420, but also along the side edges of mesh 420, which may prevent adhesions along the mesh perimeter.

Figure 5A:
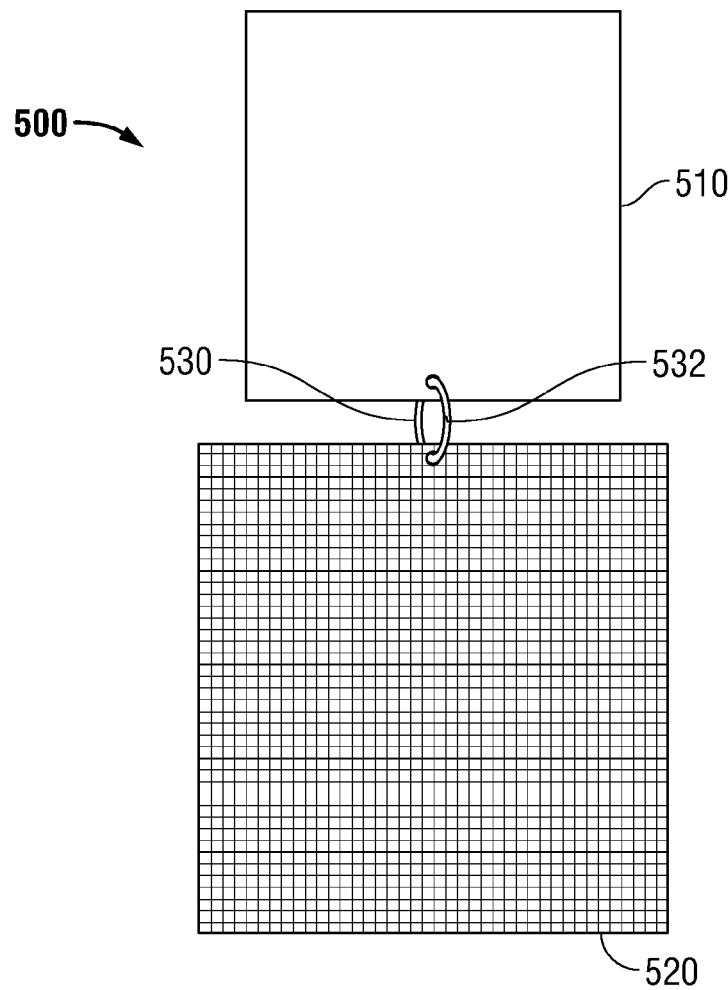
FIGS. 5A and 5B are a top view and side view, respectively, of an implantable medical device a second open position according to one embodiment described in the present disclosure.
Figure 5B:
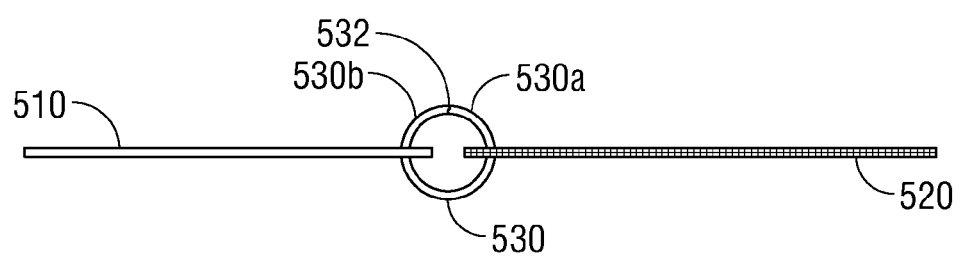

Turning now to FIGS. 5A and 5B, device 500 include film 510 pivotably connected to mesh 520 via pivot member 530. Pivot member 530 is shown in this embodiment as an O-ring design which includes first and second ends 530a and 530b which may be designed to matingly engage to form a latch 532. Thus pivot member 530 may be manipulated and/or pinched to separate first and second ends 530a and 530b of pivot member 530 to open the O-ring thereby allowing film 510 and mesh 520 to be rotated, flipped, removed, etc.

As further shown in FIGS. 5A and 5B, in some embodiments, film 510 may be smaller in area than mesh 520. For example, film 510 may represent a central portion or band or mesh 520 and following implantation and securing of mesh 520 into tissue via sutures, staples, clips, tacks, adhesives, etc., film 510 may simply be rotated via pivot member 530 onto mesh 520 to cover the central portion of mesh 520. It is envisioned that in some embodiments, film 510 may prevent adhesion along the central portion of mesh 520. It is further envisioned that in some embodiments, film 510 may be made from a porous material which further promotes tissue ingrowth thereby further anchoring or securing device 500 into the tissue.

In some embodiments, pivot member 630, as depicted in FIGS. 6A and 6B, may pass through film 610 and/or mesh 620 more than one time to further secure film 610 to mesh 620. Pivot member 630 represents a spiral binding that runs at least along a portion of the length of film 610 and mesh 620. The spiral binding 630 strengthens the connection between film 610 and mesh 620 without reducing the ability of film 610 from pivoting. As further depicted in FIGS. 6A and 6B, in some embodiments, the shape of film 610 may differ from the shape of mesh 620. In addition, mesh 620 may include a plurality of grip members 640 on at least one side of mesh 620. In some embodiments, as illustrated in FIGS. 6A and 6B, mesh 620 may include a first portion which may be covered by film 610 and a second portion which may not be covered by film 610 and/or which may include a plurality of grip members 640. As illustrated in FIG. 6C, device 600 includes grip members 640 disposed on a side of the mesh 620, opposite side of the film 610. In alternate embodiments, grip members 640 may be disposed on the same side of the mesh 620 as the film 610.

Figure 7A:
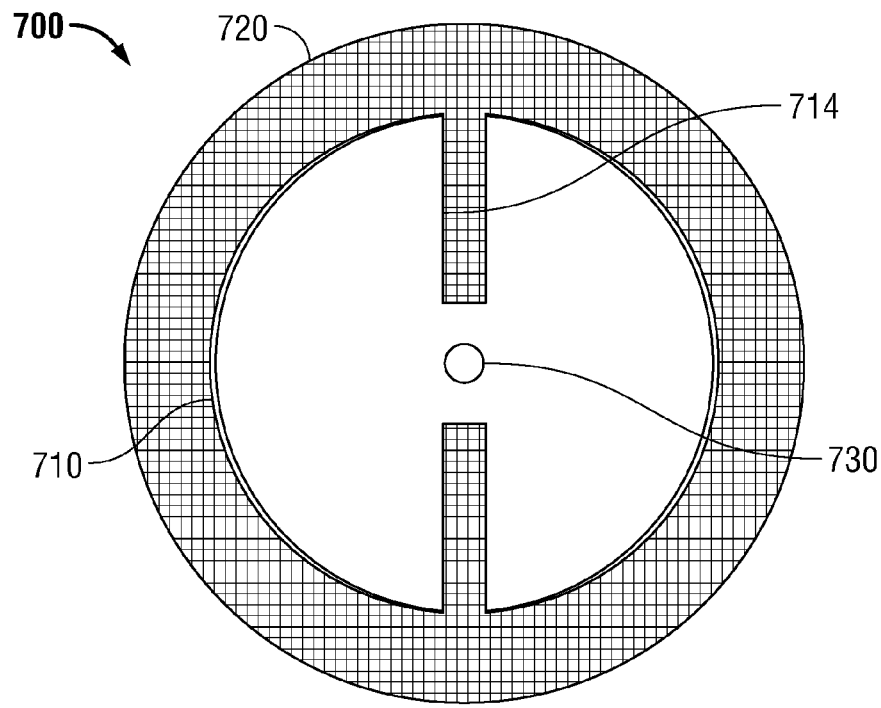
FIGS. 7A and 7B are a top view and side view, respectively, of an implantable medical device a second open position according to one embodiment described in the present disclosure.
Figure 7B:
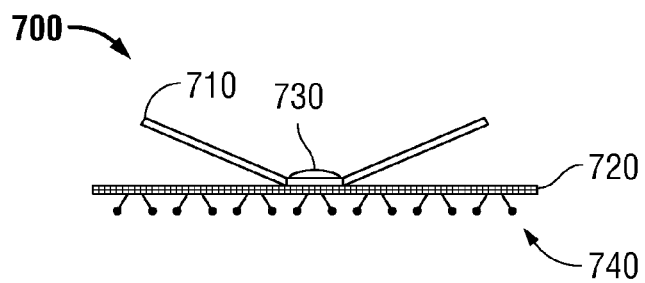

Although shown previously as generally square and/or rectangular in shape, the devices described herein including the film, the mesh and the pivot member may be of any shape. In FIGS. 7A and 7B, device 700 includes a generally circular mesh 720 pivotably connected to a generally circular film 710 via pivot member 730. Film 710 includes at least one slit 714 which provides film 710 with the flexibility to accommodate different contours commonly found in the tissue upon implantation. In some embodiments, the mesh may also include at least one slit (not shown). In addition to being pivotable to cover and uncover portions of mesh 720, film 710 may also rotate in a clockwise and/or counter clockwise direction around pivot member 730. Such movement allows slit 714 to be moved as necessary according to the tissue at the site of implantation. In addition, mesh 720 further includes grip members 740 on a side opposite film 710.

Figure 8:
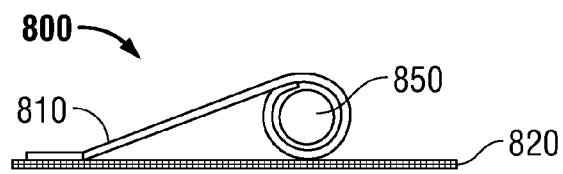
FIG. 8 is a side view of an implantable medical device according to one embodiment described in the present disclosure.

The implants described herein may be useful in many endoscopic, laparoscopic, arthroscopic, endoluminal, transluminal, and/or open surgical procedures. Some examples include hernia repair, repair of vaginal prolapse, ligament repair, tendon repair, and the like. Although the polymeric films described herein may be made from any biocompatible materials, in certain procedures, the film layers may be made from anti-adhesive materials. For example, when implanting the medical devices described herein into tissue near Cooper's ligament, it might be useful to have the flexibility to wrap around or surround the ligament, or any other sensitive tissue such as the spermatic cord, tendons, intestinal tissue, etc., as shown in FIG. 8. In FIG. 8, implant 800 includes mesh 820 pivotably attached to anti-adhesive film 810 wherein film 810 has been pivoted away from a first side of mesh 420 and wrapped around Coopers ligament 850 to prevent adhesion between the surrounding tissue and/or mesh 820 and ligament 850.

It will be understood that various modifications may be made to the embodiments disclosed herein. For example, in embodiments the medical device may rolled prior to being delivered into the body via a cannula, trocar or laparoscopic delivery device. In another example, the medical devices described herein may be sterilized and packaged into using any suitable sterilization process, i.e., gamma radiation, and any suitable medical device package, i.e., an injectable medical device package. In still other examples, the implants described herein may include more than one film, mesh, and/or pivot member. Thus, those skilled in the art will envision other modifications within the scope and spirit of the claims.

What is claimed is:

1. An implantable medical device comprising,
a mesh having at least one opening,
a film having at least one aperture, and
a pivot member positioned between the at least one opening of the mesh and the at least one aperture of the film, wherein the film is pivotably attached to the mesh via the pivot member and rotatable around the pivot member.

2. The implantable medical device of claim 1 wherein the mesh comprises a bioabsorbable material.

3. The implantable medical device of claim 1 wherein the mesh comprises a non-bioabsorbable material selected from the group consisting of polypropylene, polyethylene terephthalate, expanded polytetrafluoroethylene, condensed polytetrafluoroethylene and combinations thereof.

4. The implantable medical device of claim 1 wherein the mesh comprises polypropylene.

5. The implantable medical device of claim 1 wherein the film comprises a bioabsorbable material.

6. The implantable medical device of claim 1 wherein the film comprises polylactide.

7. The implantable medical device of claim 1 wherein the film comprises collagen.

8. The implantable medical device of claim 1 wherein the film comprises an anti-adhesion barrier.

9. The implantable medical device of claim 1 wherein the film comprises an area smaller than the mesh.

10. The implantable medical device of claim 1 wherein the film further comprises at least one therapeutic agent.

11. The implantable medical device of claim 10 wherein the therapeutic agent comprises bupivacaine.

12. The implantable medical device of claim 1 wherein the mesh further comprises at least grip member on a side opposite the film.

13. The implantable medical device of claim 1 wherein the pivot member comprises a bioabsorbable material.

14. The implantable medical device of claim 1 wherein the mesh is generally circular.

15. The implantable medical device of claim 14 wherein the film is generally circular.

16. The implantable medical device of claim 1 wherein the film further comprises at least one slit.

17. An implantable medical device comprising,
 a planar mesh,
 an anti-adhesion barrier film pivotably attached to one side of the planar mesh via a pivot member, the film including two slits, and,
 a plurality of grip members positioned on another side of the mesh opposite the film, wherein the anti-adhesion barrier film is rotatable around the pivot member.

18. The implantable medical device of claim 17 wherein the mesh comprises a non-bioabsorbable material.

19. The implantable medical device of claim 17 wherein the film comprises collagen.

20. The implantable medical device of claim 17 wherein the film comprises an area smaller than the mesh.

21. The implantable medical device of claim 17 wherein the pivot member comprises a bioabsorbable material.

* * * * *